United States Patent
Robertson et al.

(10) Patent No.: US 11,568,530 B2
(45) Date of Patent: Jan. 31, 2023

(54) SYSTEM AND METHOD TO ANALYSE AN ANIMAL'S IMAGE FOR MARKET VALUE DETERMINATION

(71) Applicant: Precision Livestock Technologies, Inc., Dallas, TX (US)

(72) Inventors: Timothy L. Robertson, Belmont, CA (US); Yashar Behzadi, Orinda, CA (US); Ricardo Alexandre Esteves Mendonca, San Jose, CA (US)

(73) Assignee: PRECISION LIVESTOCK TECHNOLOGIES, INC., Dallas, TX (US)

( * ) Notice: Subject to any disclaimer, the term of this patent is extended or adjusted under 35 U.S.C. 154(b) by 1 day.

(21) Appl. No.: 16/393,807

(22) Filed: Apr. 24, 2019

(65) Prior Publication Data
US 2020/0202511 A1 Jun. 25, 2020

Related U.S. Application Data

(63) Continuation-in-part of application No. 16/231,283, filed on Dec. 21, 2018, now abandoned.

(51) Int. Cl.
| | |
|---|---|
| *G06T 7/00* | (2017.01) |
| *G06N 20/00* | (2019.01) |
| *G16H 30/40* | (2018.01) |
| *G06T 7/11* | (2017.01) |
| *G06V 40/10* | (2022.01) |
| *G06Q 30/02* | (2012.01) |
| *G06K 9/62* | (2022.01) |

(52) U.S. Cl.
CPC .......... *G06T 7/0004* (2013.01); *G06K 9/6255* (2013.01); *G06N 20/00* (2019.01); *G06Q 30/0283* (2013.01); *G06T 7/11* (2017.01); *G06V 40/10* (2022.01); *G16H 30/40* (2018.01); *G06T 2207/20081* (2013.01); *G06T 2207/30128* (2013.01)

(58) Field of Classification Search
None
See application file for complete search history.

(56) References Cited

U.S. PATENT DOCUMENTS

| | | | |
|---|---|---|---|
| 8,950,361 | B1 | 2/2015 | Pierce |
| 9,940,711 | B2 * | 4/2018 | Bregman-Amitai ........................ G06T 7/0012 |
| 10,593,041 | B1 * | 3/2020 | Shaw ................... G06K 9/6256 |
| 2010/0104203 | A1 * | 4/2010 | Garakani ............... G06V 20/40 382/228 |
| 2010/0118149 | A1 * | 5/2010 | Levin ..................... G06Q 10/06 348/169 |
| 2013/0034624 | A1 * | 2/2013 | Gorocica Buenfil ........................ A01K 67/027 426/2 |
| 2013/0155235 | A1 * | 6/2013 | Clough ................ G06K 9/6223 382/110 |

(Continued)

*Primary Examiner* — Nancy Bitar
(74) *Attorney, Agent, or Firm* — Dana Legal Services; Jubin Dana

(57) ABSTRACT

A system and method are disclosed for training a system or a model to allow estimation of the value of livestock that is farmed for monetary gain. The various aspects of the invention include generation of data that is used to supplement or augment capture or real data, wherein the subject of the data is an animal. Labels or attributes are generated and validated.

9 Claims, 3 Drawing Sheets

(56) References Cited

U.S. PATENT DOCUMENTS

| | | | |
|---|---|---|---|
| 2014/0088939 A1* | 3/2014 | Garant | G06Q 30/018 |
| | | | 703/2 |
| 2016/0050888 A1 | 2/2016 | Berckmans et al. | |
| 2017/0086429 A1 | 3/2017 | Horton et al. | |
| 2017/0118961 A1 | 5/2017 | Halachmi et al. | |
| 2019/0021292 A1* | 1/2019 | Hayes | A01K 63/06 |
| 2019/0156151 A1* | 5/2019 | Wrenninge | G06K 9/6256 |
| 2019/0340440 A1* | 11/2019 | Atwater | A01K 61/13 |
| 2020/0090627 A1* | 3/2020 | Saito | G06T 19/00 |
| 2020/0202511 A1* | 6/2020 | Robertson | G06Q 30/0283 |

\* cited by examiner

SYSTEM AND METHOD TO ANALYSE AN ANIMAL'S IMAGE FOR MARKET VALUE DETERMINATION

CROSS REFERENCE TO RELATE APPLICATION

This application is a continuation-in-part of and claims priority to U.S. Non-Provisional application Ser. No. 16/231,283 filed on 21 Dec. 2018 with titled SYSTEM AND METHOD FOR CONTROLLING ANIMAL FEED by Timothy L. ROBERTSON et al., the entire disclosure of which is incorporated herein by reference.

FIELD OF THE INVENTION

The invention is in the field of computer systems and, more specifically, related to using synthetic data with real data in analysis of images of animals.

BACKGROUND

Artificial Intelligent System (AIS) are trained system that perform a specific task. For example, an AIS can be used to recognize a subject when the AIS is trained to recognize the subject using training data. Currently, known methods of training AIS include using captured data that is labeled or tagged. However, using data to train an AIS or any similar system can take a long time, especially when it comes to animals. Furthermore, there currently is no efficient method for controlling or generating the training data needed to train an AIS for recognition of animals that are farmed for financial gain. Therefore, what is needed is a system and method that allows generation of training data that can be used to train a system in a short period of time and with a high degree of control over variations in the training data.

SUMMARY OF THE INVENTION

The invention discloses a system and method for training a system in a short period of time using training data with animals as the subject. The various aspects of the invention include generation of synthetic data that is used to supplement or augment capture or real data. The system can be trained using the synthetic data, wherein there is a high degree of control over each of the parameters that can be varied to generate the synthetic data. There are labels or attributes generated for the real data. Those labels are validated. The labels can be used with the generated synthetic data. The generated synthetic data is generated by alterations or variations in the captured or real data as well as using purely synthetic data generated using computers. In accordance with the various aspects of the invention, the synthetic data is used to supplement, enhance or augment real data. This results in a combined data set that can be quickly and easily generated. The combined data set is used to train the model or artificial intelligence system (AIS). Then the trained model is used on newly generated data, which can be synthetic, real, or a combination thereof, to infer or generate the appropriate labels or attributes for the subject of the newly generated data.

DETAILED DESCRIPTION

To the extent that the terms "including", "includes", "having", "has", "with", or variants thereof are used in either the detailed description and the claims, such terms are intended to be inclusive in a similar manner to the term "comprising". The invention is described in accordance with the aspects and embodiments in the following description with reference to the FIGs., in which like numbers represent the same or similar elements.

The ranges of values provided herein do not limit the scope of the present invention. It is understood that each intervening value, between the upper and lower limit of that range and any other stated or intervening value in that stated range, is encompassed within the scope of the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Figure 1:
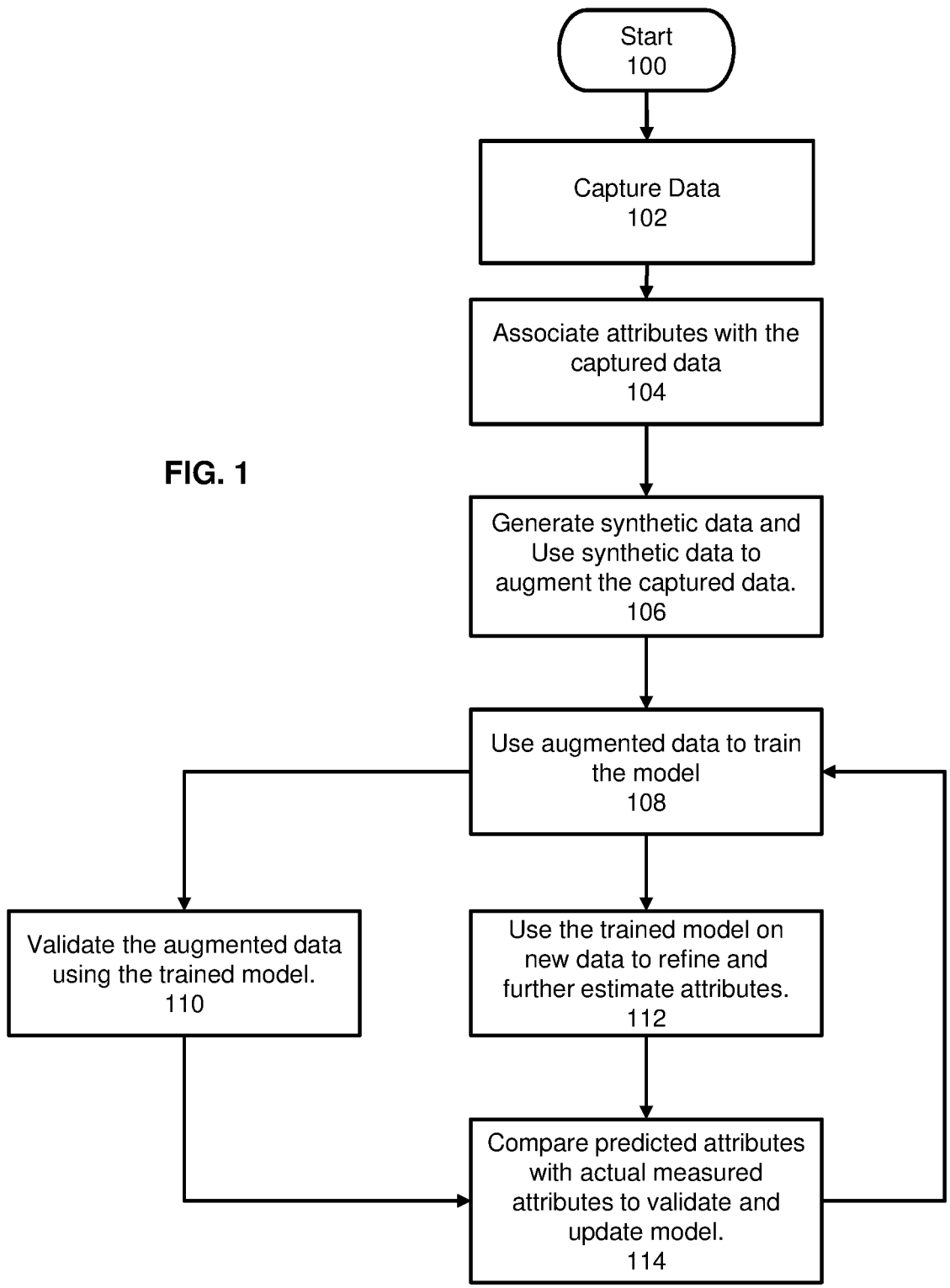
FIG. 1 shows a process for using synthetic data to supplement real data in accordance with the various aspects and embodiments of the invention.

Referring now to FIG. 1, the process 100 for supplementing or augmenting real data is shown. At step 102 data (or real data) is captured. The label "captured" is used in relation to real data and the real data may come from any source, including video as well as dynamic images and static images. Captured data may also be real objects in any setting or environment, including naturally occurring or unnatural environment. For example, a tree is naturally found outdoors, which is a natural environment for the tree. A tree may also be planted in a pot and located indoors, which is an unnatural environment for the tree. A cow is naturally found outdoors in a pasture. The same cow same also be standing in a living room next to a table, which is an unnatural environment for the cow. The captured data includes various content or images.

In accordance with one embodiment, the captured data is an image that includes, at least, an image of an animal. As used herein, the term "animal" includes livestock that is raised for the purpose of profit. For example, animal includes at least cattle, pigs, poultry, horses, birds, insects, and fish. Animal also includes animals farmed for consumption, such as beef cattle, poultry, and aquaculture. Animal also includes animals farmed to produce a product for consumption, such as dairy cattle or eggs from poultry.

The captured data may include data tags that are specific to the animal in the capture image. Examples of the types of data that is specific to an anima include: breed, gender, age, etc. for the animal. In accordance with an aspect of the invention, the capture data includes information about environmental setting and geometry, such as camera angle, distance from the camera position, background natural and artificial lighting, or information about the object that makes-up the content of the captured data. In accordance with the various aspects of the invention, the capture data, which includes the animal as a subject, may include other information, such as objects in the background environment and background lighting.

At step 104, various attributes or labels are associated with the captured data. In accordance with the various aspects of the invention, attributes include any number of measurable parameters. For example, in accordance with an aspect of the invention, the capture data includes an image of the animal and the various attributes, which are associated with the animal in the photo, include weight, height, bone structure, body composition in terms of fat:muscle ratio, physical health, behavior, mental health, etc. The scope of the invention is not limited by the foregoing articulated list of attributes, as there are many different attributes that can be defined, measured, and quantified as outline below.

At step 106 synthetic data is generated and used to supplement or augment the capture data. Given the attributes associated with the capture data, in accordance with one aspect of the invention, synthetic data is generated by altering the various attributes of the captured data. Each alteration to any attribute can be used to generate a different synthetic image. For example, shapes or sizes of the animal in the captured image can be varied by altering the attributes. In accordance with one aspect of the invention, lighting intensity (or any parameter associated with lighting conditions) is varied to generate the different or new synthetic data.

In accordance with an aspect of the invention, synthetic data that is based on anatomy is used and generated to model parameters of various anatomy or underlying anatomy of the object. For example, for an animal, the model uses real data based on images of anatomy or generates anatomical synthetic data. The data represents various parameters, for example parameterization of the bone length and muscle size. The model can add or combine the data with newly generated synthetic data that is based on the anatomy characteristics. For example, synthetic data is generated to represent the skin. The model can combine the synthetic data (synthetic skin) with the data (anatomic data) by draping the synthetic skin over the anatomy data to generate a new synthetic image. In accordance with an aspect of the invention, physiological parameters supplement the data, which parameters include blood characteristics and blood vessel properties. In this example, the physiological parameters are provided as input to the model and help the model generate (or select) the color for the synthetic skin that will be used in the new synthetic image generated by the model. As such, the model can generate or build or complete real data (real images) and synthetic data (synthetic images) using anatomical parameters.

At step 108, the synthetic data supplements or augments the captured data. The resulting data set, which includes both synthetic and captured data, is used for further train the model. The overall system is able to be trained faster because the quantity of synthetic data that can be generated and used to train and develop the model. The model may include any artificial intelligent system.

At step 110, the synthetic data used to augment the captured data is validated. For example, the synthetic data is fed to the model that is part of the system. The synthetic data is reviewed and labeled by the model. The labels associated with the synthetic data, which includes the various attributes, can then be reviewed and used to confirm the validity of the synthetic data.

At step 112, the trained model is used on new data, which may be captured data or synthetic data, to determine future attributes. In this way the system can predict the future attributes of objects that appear in the data. For example, consider the aspect of the invention wherein the captured data includes an image of an animal. The image can be an actual image captured or the image can be synthetically generated. The model can analyze the image. The model can provide predictions of any attribute associated with the animal in the image. For example, the model can predict the animal's future weight, height, body composition, or health.

For example, when the subject animal is a calf, the model can predict future attributes of the calf based on the current image. The model, for example, can provide information about the current body composition of the animal, at what point-in-time in the future the animal will be at optimal weight for purpose of selling the animal, what behavior characteristics the animal will display as an adult, etc. The various aspects of the invention include monitoring individual animal characteristics, using the attributes or labels, to allow optimization of animal product production. In this way, the market value of an animal can be analyzed at the animal's early stages. The system would be provided with current image of the animal. The model would analyze the images to predict future attributes about the animal. Then, as the animal develops and grows, there are attributes or labels that can be monitored and measured. The monitored and measured attributes or labels can be compared to the predicted or infer attributes or labels. The economic value of an animal, as inferred can be compared to actual measured values and feed back to system to further train and develop the model or system. For example, analyzing an image of a cow, the model can use labels or attributed for the cow in the image that are associated with the various cuts of meat and composition to estimate the actual or future value of the cow, the time-to-market for the cow, the feed requirements to achieve the desired growth, and the time-to-market to achieve the economic return or value desired.

At step 114, once the future attributes of the animal are provided, the future predicted attributes can be tracked overtime. The predicted values can then be compared to actual measure future values for the specific animal. The predicted values, when compared to the future measured values, can then be further confirmed and validated. The validation, based on the comparison, can be fed back to the model to further train and update the model's accuracy. Thus, the longer the model operates and tracks information about the captured data, the more accurate the model becomes in predicting future attributes.

Figure 2:
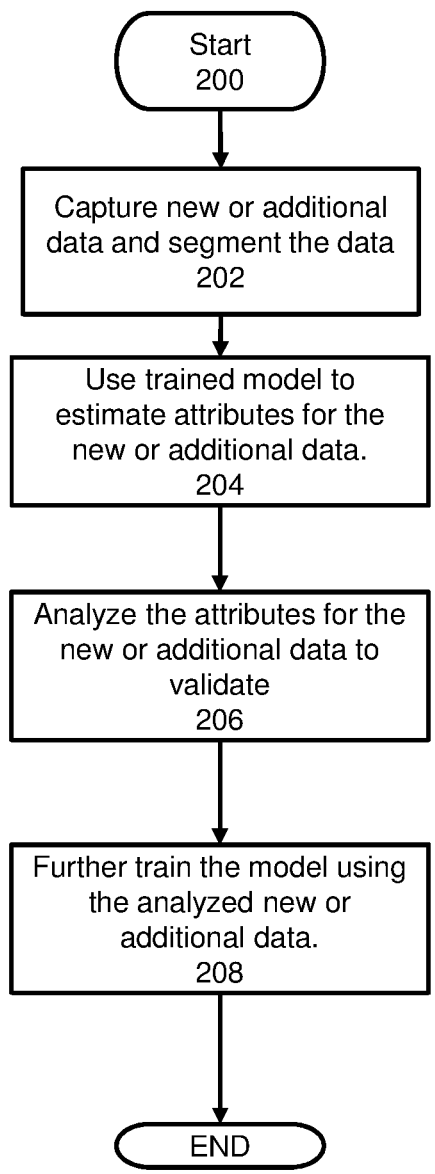
FIG. 2 shows a process for estimating attributes in accordance with the various aspects and embodiments of the invention.

Referring now to FIG. 2, the process 200 for predicting future attributes based on captured data or generated synthetic data is shown. The synthetic data is the new data that is generated for improving model performance as well as training the model. At step 202, newly captured data or additional new synthetic data is provided to the model. The model receives the data. The model segments the data in order to identify the objects or objects in the data that the model will analyze. At step 204, the model estimates attributes that are associated with the object. At step 206 the model analyzes the estimated attributes for the object identified in the data in order to validate the estimation. At step 208, the model uses the validated estimation for the data in order to further train or update the train model. In accordance with the aspects of the invention, various attributes or labels, for a specific animal, are tracked and monitored over a period of time, which can range from a few days to several years.

Figure 3:
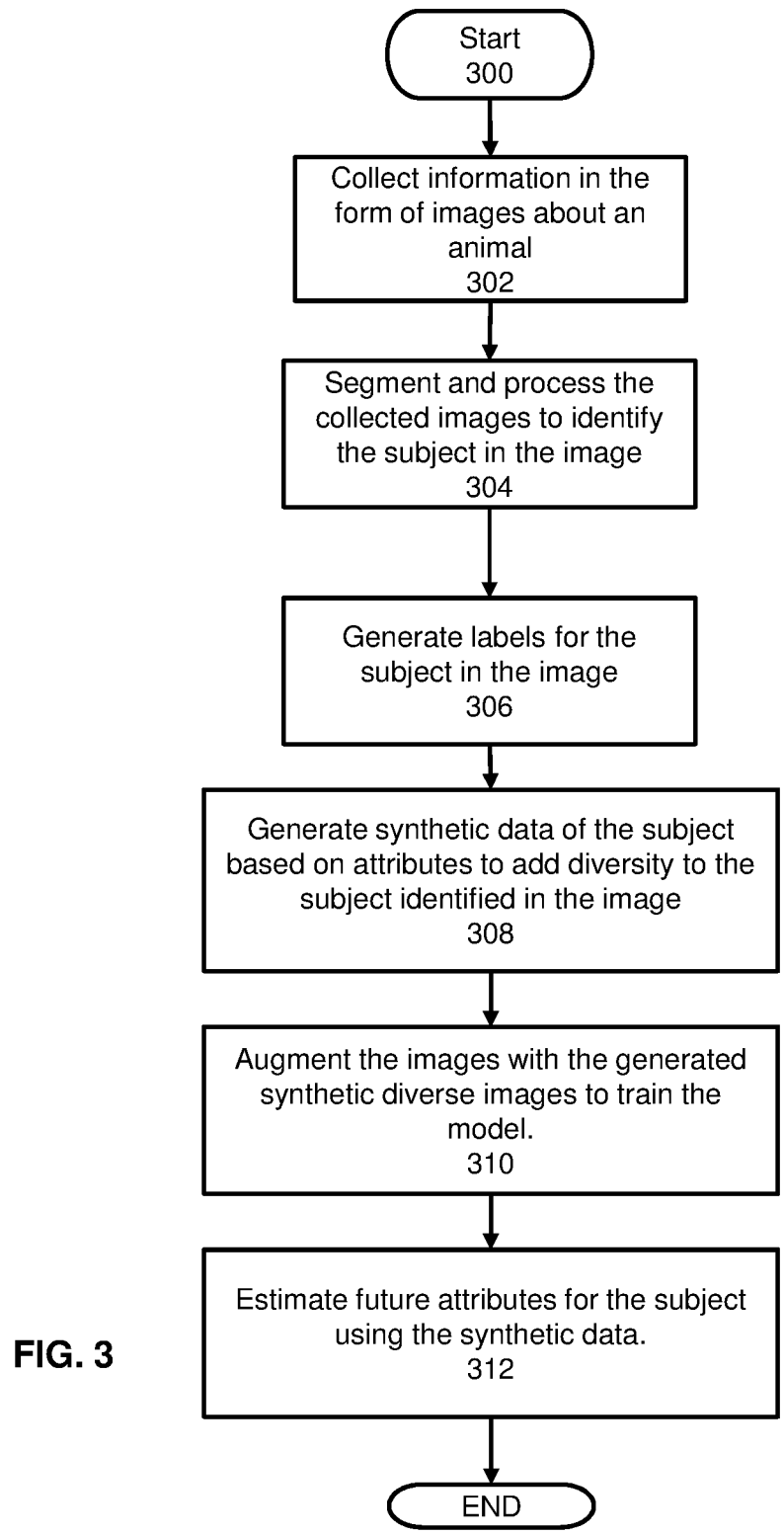
FIG. 3 shows a process for segmenting images to generate synthetic data in accordance with the various aspects and embodiments of the invention.

Referring now to FIG. 3, the process 300 for segmenting images is shown. At step 302 information is collected in the form of images. In accordance with the aspects of the invention, the images are collected using any known method of image generation, such as with a video camera, a still image camera, instantaneous captured images from a video segment, computer generated images, etc. Thus, the scope of the invention is not limited by the source of the image or type of image generated. In accordance with an aspect of the invention, the image includes an image of an animal. While reference is made to an animal, as noted above, an animal includes a fish, an insect, or a bird. The scope of the invention is not limited by the subject in the data or image.

At step 304, the captured data or image are segmented to identify the subject of the analysis. For example, if the subject is a cow in the data or image, then the segmentation of the image allows for separation of the cow from the remainder of the image. At step 306, attributes or labels are generated for the subject of the image. For example, the labels or attributes for the subject of a cow include: height, weight, body composition, dimensions of the limbs, etc. Similar attributes can be included for different animals in accordance with other aspects of the invention.

At step 308, using the labels provided, the synthetic images of the subject are generated. By altering the labels or attributes of the subject in the image, a diverse set of synthetic data can be created. This allows augmentation of the data with synthetic images, each synthetic image of the subject having its own unique set of attributes or labels. At step 310, augmented images that include the attributes of the system are provided to the model. The model further trained using the synthetically generated diverse images of the selected subject. As step 312, the trained model estimates future attributes for the subject. The system can then generate images, based on the future attributes, with future prediction of the subject. For example, various predictions can be determined for the subject and images generated to represent the animal, especially as related to how the animal grows and the conditions needed to ensure optimal growth of the animal.

The attributes discussed herein are only representative examples of the types of parameters that can be measured and/or tracked. Any number of attributes can be measured. For example, as related to physical conditions, the facial expressions of the animal, the condition of the ears, the order in terms of pack leaders and followers, dominance, feeding order, etc. All of these physiological conditions can be captured, generated, or altered using the system.

In accordance with some aspects of the invention, the model can be used for determining optimal environmental condition to ensure that the animals are living in optimal conditions for growth and development, including the mental state of the animal. For example, how the animals are separated and sorted is one attribute that can be predicted, measured, and controlled to impact the animal's overall growth, development and health, which has an impact on the market value of the animal.

Accordingly, the preceding merely illustrates the various aspects and principles as incorporated in various embodiments of the invention. It will be appreciated that those of ordinary skill in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

Reference throughout this specification to "one embodiment," "an embodiment," or "in accordance with some aspects" and similar language means that a particular feature, structure, or characteristic described in connection with the various aspects and embodiments are included in at least one embodiment of the invention. Thus, appearances of the phrases "in accordance with an aspect," "in accordance with one embodiment," "in an embodiment," "in certain embodiments," and similar language throughout this specification refer to the various aspects and embodiments of the invention. It is noted that, as used in this description, the singular forms "a," "an" and "the" include plural referents, unless the context clearly dictates otherwise.

The described features, structures, or characteristics of the invention may be combined in any suitable manner in accordance with the aspects and one or more embodiments of the invention. In the following description, numerous specific details are recited to provide an understanding of various embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring the aspects of the invention.

In accordance with the teaching of the invention a computer and a computing device are articles of manufacture. Other examples of an article of manufacture include: an electronic component residing on a mother board, a server, a mainframe computer, or other special purpose computer each having one or more processors (e.g., a Central Processing Unit, a Graphical Processing Unit, or a microprocessor) that is configured to execute a computer readable program code (e.g., an algorithm, hardware, firmware, and/or software) to receive data, transmit data, store data, or perform methods.

Additionally, it is intended that such equivalents include both currently known equivalents and equivalents developed in the future, i.e., any elements developed that perform the same function, regardless of structure. The scope of the invention, therefore, is not intended to be limited to the exemplary embodiments shown and described herein.

Unless defined otherwise, all technical and scientific terms used herein have the same meaning as commonly understood by one of ordinary skill in the art to which this invention belongs. The verb couple, its gerundial forms, and other variants, should be understood to refer to either direct connections or operative manners of interaction between elements of the invention through one or more intermediating elements, whether or not any such intermediating element is recited. Any methods and materials similar or equivalent to those described herein can also be used in the practice of the invention. Representative illustrative methods and materials are also described.

An article of manufacture or system, in accordance with various aspects of the invention, is implemented in a variety of ways: with one or more distinct processors or microprocessors, volatile and/or non-volatile memory and peripherals or peripheral controllers; with an integrated microcontroller, which has a processor, local volatile and non-volatile memory, peripherals and input/output pins; discrete logic which implements a fixed version of the article of manufacture or system; and programmable logic which implements a version of the article of manufacture or system which can be reprogrammed either through a local or remote interface. Such logic could implement a control system either in logic or via a set of commands executed by a processor.

All publications and patents cited in this specification are herein incorporated by reference as if each individual publication or patent were specifically and individually indicated to be incorporated by reference and are incorporated herein by reference to disclose and describe the methods and/or system in connection with which the publications are cited. The citation of any publication is for its disclosure prior to the filing date and should not be construed as an admission that the invention is not entitled to antedate such publication by virtue of prior invention. Further, the dates of publication provided may be different from the actual publication dates which may need to be independently confirmed.

Therefore, the scope of the invention is not intended to be limited to the various aspects and embodiments discussed and described herein. Rather, the scope and spirit of invention is embodied by the appended claims.

What is claimed is:

1. A non-transitory computer readable medium including code that, when executed by at least one processor in a system, would cause the system to:
   associate a plurality of attributes with real collected data for a growing animal, wherein the real collected data includes at least one current image of the growing animal;
   generate a synthetic data set using the plurality of attributes, wherein the synthetic data set includes synthetic images of the growing animal;
   add the synthetic data set to a training data set, which includes the real collected data, to produce a new training data set;
   use the new training data set as training data to train a model;
   analyze, using the model, the current image of the growing animal to predict future attributes for the growing animal;
   estimate economic value of the growing animal using the analyzed current images;
   provide feedback to the model by comparing the predicted future attributes to actual future measured attributes to update the new training data set;
   predict an anatomical parameter for the growing animal using existing anatomical parameters;
   generate an anatomical synthetic image; and
   combine the anatomical synthetic image with the current image of the growing animal to generate a new animal synthetic image.

2. The non-transitory computer readable medium of claim 1 further including code that, when executed, causes the system to segment the current image to isolate the portion that contains the growing animal.

3. The non-transitory computer readable medium of claim 2, wherein the synthetic data is generated by altering at least one characteristic of the growing animal.

4. The non-transitory computer readable medium of claim 3 further including code that, when executed, causes the system to estimate an attribute of the growing animal based on the synthetic data generated by altering the characteristic, wherein the attribute estimation allows time-based attribute determination associated with the growing animal.

5. The non-transitory computer readable medium of claim 4, wherein the attribute includes at least one attribute selected from the group of attributes including weight, body composition, height, behavior, breed, gender, age, and health.

6. The non-transitory computer readable medium of claim 4 further including code that, when executed, causes the system to:
   validate the new training data set to produce validated data; and
   use the validated data to train the model.

7. The non-transitory computer readable medium of claim 6 further including code that, when executed, causes the system to:
   display the future attributes on a display to a user, thereby allowing the user to determine time-to-market for the growing animal.

8. A method for generating synthetic data sets that are used in training a model that predicts future size to determine future market value of a growing animal, the method comprising:
   selecting a plurality of anatomic parameters that are present in a real image of the growing animal;
   identifying a new parameter that is related to the growing animal found in the real image, wherein the new parameter is different from the plurality of anatomic parameters;
   generating a synthetic data set, which is based on the plurality of anatomic parameters, including at least one synthetic anatomical image using the new parameter that represent a future size of the growing animal;
   building a training data set, which includes the synthetic data set and the real image, used to train the model;
   analyzing, using the model, the real image of the growing animal to predict future size of the growing animal;
   updating the training data set for the model by comparing the predicted future size to an actual future measured size of the growing animal;
   predict an anatomic parameter for the growing animal based on the selected plurality of anatomic parameters;
   generate an anatomical synthetic image;
   combine the anatomical synthetic image with a current image of the growing animal to generate a new animal synthetic image; and
   estimating economic value of the growing animal using the analyzed real image of the growing animal and the new animal synthetic image.

9. The method of claim 8, wherein the new parameter is at least one of a blood characteristic and blood vessel.

* * * * *